(12) United States Patent
Mitra et al.

(10) Patent No.: US 11,266,421 B2
(45) Date of Patent: Mar. 8, 2022

(54) ROBOTICALLY ASSISTED BONE PREPARATION FOR POSITIONING OF CUTTING BLOCK

(71) Applicant: Smith & Nephew, Inc., Memphis, TN (US)

(72) Inventors: Riddhit Mitra, Pittsburgh, PA (US); Samuel Dumpe, Beaver, PA (US); Branislav Jaramaz, Pittsburgh, PA (US); David Davidson, Pittsburgh, PA (US)

(73) Assignee: Smith & Nephew, Inc., Memphis, TN (US)

( * ) Notice: Subject to any disclaimer, the term of this patent is extended or adjusted under 35 U.S.C. 154(b) by 47 days.

(21) Appl. No.: 16/651,457

(22) PCT Filed: Oct. 1, 2018

(86) PCT No.: PCT/US2018/053752
§ 371 (c)(1),
(2) Date: Mar. 27, 2020

(87) PCT Pub. No.: WO2019/068088
PCT Pub. Date: Apr. 4, 2019

(65) Prior Publication Data
US 2020/0281607 A1 Sep. 10, 2020

Related U.S. Application Data

(60) Provisional application No. 62/565,860, filed on Sep. 29, 2017.

(51) Int. Cl.
*A61B 17/16* (2006.01)
*A61B 17/92* (2006.01)
(Continued)

(52) U.S. Cl.
CPC ...... *A61B 17/1604* (2013.01); *A61B 17/1675* (2013.01); *A61B 17/1764* (2013.01);
(Continued)

(58) Field of Classification Search
CPC ............ A61B 17/1604; A61B 17/0682; A61B 17/0684; A61B 2017/922; A61B 2017/925
See application file for complete search history.

(56) References Cited

U.S. PATENT DOCUMENTS

| | | | |
|---|---|---|---|
| 6,205,411 B1 | 3/2001 | DiGioia, III et al. | |
| 6,757,582 B2 | 6/2004 | Brisson et al. | |
| 2010/0076440 A1* | 3/2010 | Pamichev | A61B 17/1604 606/79 |

FOREIGN PATENT DOCUMENTS

| | | |
|---|---|---|
| EP | 2502581 A1 | 9/2012 |
| EP | 2959852 A1 | 12/2015 |

OTHER PUBLICATIONS

International Search Report and Written Opinion for PCT/US2018/053752 dated Apr. 1, 2019.

* cited by examiner

*Primary Examiner* — Samuel S Hanna
(74) *Attorney, Agent, or Firm* — Troutman Pepper Hamilton Sanders LLP

(57) ABSTRACT

Surgical punch tools and methods of using the same are disclosed herein. A surgical punch tool may include a stationary base component having a planar bottom side. The planar bottom side may include one or more posts extending therefrom. Each post may include an associated sharp pin. A movable actuation portion may be configured to move each sharp pin from a non-actuated position within the corre- (Continued)

sponding post to an actuated position extending through the base component and from the corresponding post.

8 Claims, 10 Drawing Sheets

(51) Int. Cl.
  *A61B 34/20* (2016.01)
  *A61B 34/30* (2016.01)
  *A61B 17/17* (2006.01)
(52) U.S. Cl.
  CPC .............. *A61B 34/20* (2016.02); *A61B 34/30* (2016.02); *A61B 2034/2055* (2016.02); *A61B 2034/2065* (2016.02)

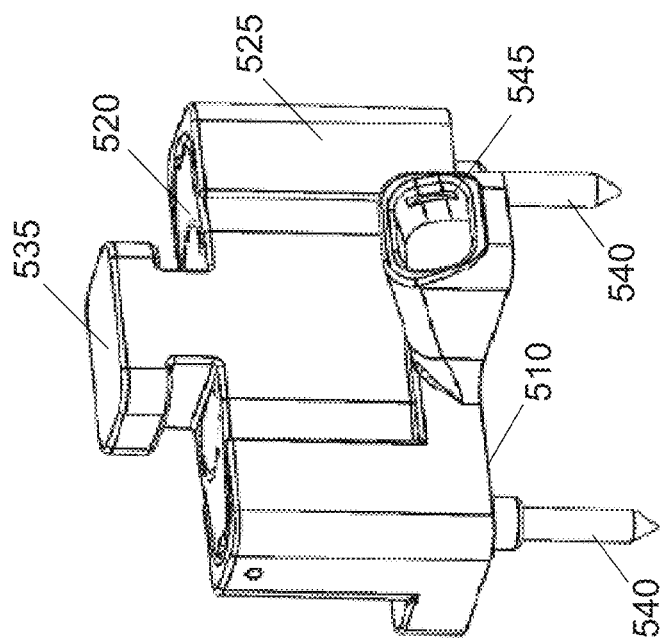
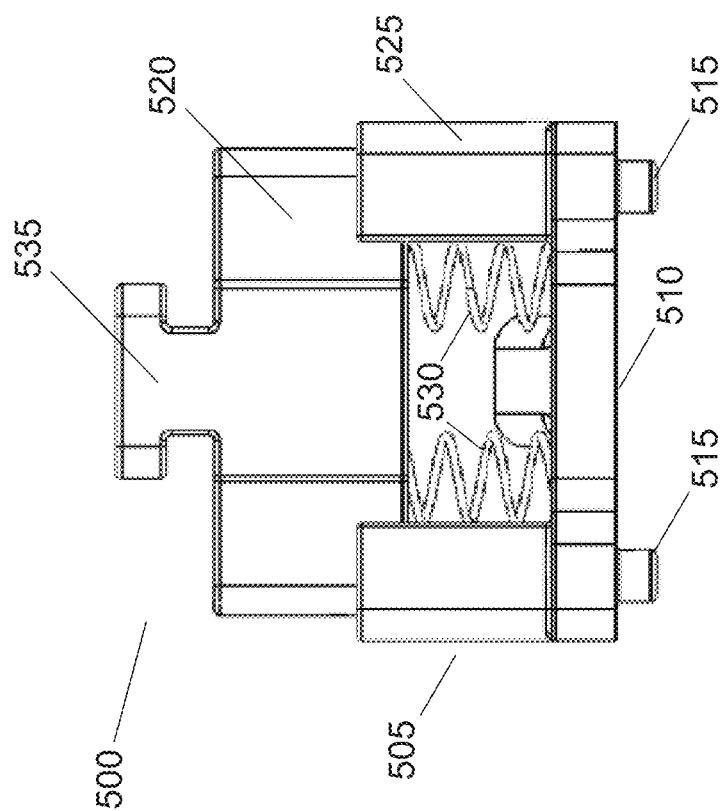

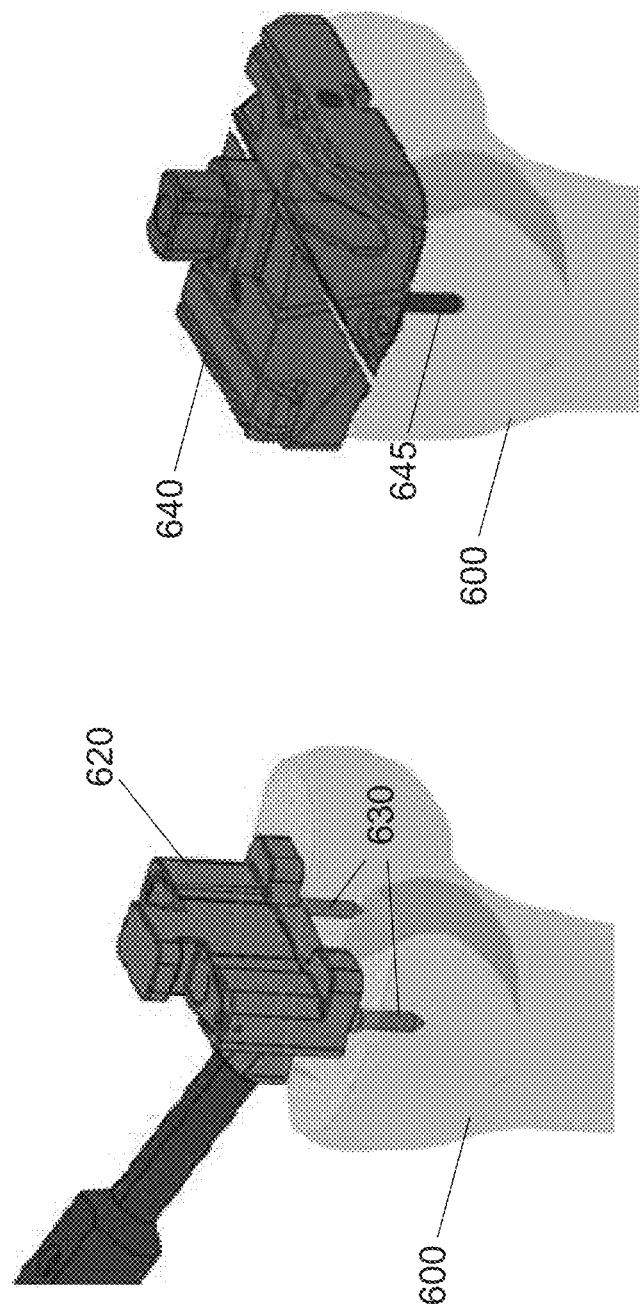

ROBOTICALLY ASSISTED BONE PREPARATION FOR POSITIONING OF CUTTING BLOCK

CLAIM OF PRIORITY

This patent application is a national stage application of International Patent Application No. PCT/US2018/053752, titled "ROBOTICALLY ASSISTED BONE PREPARATION FOR POSITIONING OF CUTTING BLOCK," filed on Oct. 1, 2018, which claims the benefit of priority of U.S. Provisional Patent Application Ser. No. 62/565,860, titled "Robotically Assisted Bone Preparation for Positioning of Cutting Block," filed on Sep. 29, 2017, each of which is hereby incorporated by reference herein in its entirety.

TECHNICAL FIELD

The present disclosure generally relates to the use of robotic systems in planning and performing orthopedic implant surgical procedures. More specifically, the present disclosure relates to using robotic systems to guide bone resection for more efficient placement of a cutting block.

BACKGROUND

The use of computers, robotics, and imaging to aid orthopedic surgery is well known in the art. There has been a great deal of study and development of computer-aided navigation and robotics systems used to guide surgical procedures. For example, a precision freehand sculptor (PFS) employs a robotic surgery system to assist the surgeon in accurately cutting a bone into a desired shape. In interventions such as total knee replacement, computer-aided surgery techniques have been used to improve the accuracy and reliability of the surgery.

A cut guide can be used in an orthopedic surgery to assist a surgeon in cutting or modifying some portions of a target bone. For example, in joint replacement surgeries, such as total hip replacement (THR) or total knee replacement (TKR), a cut guide can be temporarily attached to the target bone such as a femur or a tibia. An orthopedic surgical cutting tool can be used together with the cut guide to allow the surgeon to selectively cut portions of the ends of the target bone and replace them with endoprosthetic implants. Positioning a cut guide for use in preparing the target bone can be a time-consuming and complicated process, which is critical to positive outcomes for the patient.

SUMMARY

There is provided a surgical punch tool that includes a stationary base component having a planar bottom side, one or more posts extending from the planar bottom side, one or more sharp pins each associated with a corresponding post, and a movable actuation portion configured to move each sharp pin from a non-actuated position within the corresponding post to an actuated position extending through the base component and from the corresponding post.

In some embodiments, the base component further includes a plurality of channels configured to receive and guide the actuation portion.

In some embodiments, the surgical punch tool further comprises one or more devices configured to provide a biasing force opposing movement of the actuation portion towards the base component. In some embodiments, the surgical punch tool further comprises one or more devices configured to provide a biasing force promoting movement of the actuation portion towards the base component. In some embodiments, the one or more devices comprise at least one spring. In some embodiments, the surgical punch tool further includes a catch configured to secure the sharp pins in the non-actuated position, and a release mechanism configured to release the catch from securing the sharp pins in the non-actuated position.

In some embodiments, the actuation portion comprises an impact face configured to receive an impact force that causes the sharp pins to move from the non-actuated position to the actuated position.

In some embodiments, each of the one or more posts extends from the base by about 2.5 mm to about 5 mm. In some embodiments, each of the one or more posts has a diameter of about 5 mm to about 7.5 mm. In some embodiments, each of the one or more sharp pins extends from the base by about 15 mm to about 20 mm in the actuated position. In some embodiments, each of the one or more sharp pins has a diameter of about 2.5 mm to about 4 mm. In some embodiments, the one or more sharp pins comprise a first sharp pin and a second sharp pin, and a center of the first sharp pin is about 1.25 inches to about 1.75 inches away from a center of the second sharp pin.

There is also provided a method of preparing a target bone to receive a cut guide. The method includes selecting a punch tool corresponding to the cut guide. The punch tool comprises a plurality of sharp pins and a movable actuation portion configured to move each sharp pin from a recessed position to an extended position. The method further includes resecting the target bone, positioning the punch tool with respect to the resected target bone, and actuating the actuation portion of the punch tool to move the plurality of sharp pins from the recessed position to the extend position, whereby each of plurality of sharp pins forms a hole in the target bone.

In some embodiments, the cut guide comprises a first mounting pin and a second mounting pin, the first mounting pin is spaced apart from the second mounting pin by a distance, the plurality of sharp pins comprises a first sharp pin and a second sharp pin, and the first sharp pin is spaced apart from the second sharp pin by the distance.

In some embodiments, resecting the target bone comprises forming, using a robotically assisted cutting tool, a distal plane in the target bone, and forming, using a robotically assisted cutting tool, a plurality of divots in the distal plane, wherein the plurality of divots are configured to receive the punch tool. In some embodiments, each of the plurality of divots has a recessed portion, and each recessed portion is in a shape of one of a cylinder, a cube, a rectangular prism, a triangular prism, a pyramid, and a cone. In some embodiments, positioning the punch tool comprises positioning the punch tool such that each of the plurality of sharp pins is vertically aligned with one of the plurality of divots.

In some embodiments, resecting the target bone comprises forming, using a robotically assisted cutting tool, a distal plane in the target bone, and positioning the punch tool comprises tracking a position of the punch tool with a surgical tracking system.

In some embodiments, actuating the actuation portion of the punch tool comprises applying an impact force to the actuation portion of the punch tool.

In some embodiments, actuating the actuation portion comprises releasing a catch configured to retain the actuation portion in a position such that the plurality of sharp pins are in the recessed position.

There is also provided a method of preparing a target bone to receive a cut guide. The method includes receiving, by a surgical system, an indication of the cut guide to use with the target bone and determining, by the surgical system, a punch tool associated with the cut guide. The punch tool comprises a plurality of sharp pins and a movable actuation portion configured to move each sharp pin from a recessed position to an extended position. The method further includes determining, by the surgical system, a portion of the target bone to resect based on the cut guide, controlling, by the surgical system, the operation of a cutting device based on the determined amount and location of the target bone to resect, directing, by the surgical system, placement of the punch tool within the resected target bone, and directing, by the surgical system, actuation of the actuation portion of the punch tool.

In some embodiments, controlling the operation of the cutting device comprises tracking, by the surgical system, the location and orientation of the cutting device, and activating, by the surgical system, the cutting tool when the cutting tool is in proximity to the portion of the target bone to resect.

The example embodiments as described above can provide various advantages over prior techniques. For example, the techniques as taught herein can more quickly and precisely position a cut guide during a surgical implant procedure. As such, the techniques taught herein provide better patient outcomes resulting from reduced operation times and better placed implants.

Further features and advantages of at least some of the embodiments of the present disclosure, as well as the structure and operation of various embodiments of the present disclosure, are described in detail below with reference to the accompanying drawings.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the present disclosure. In the drawings:

FIGS. 5A and 5B depict multiple views of a punch guide for aiding in cut guide attachment in accordance with an embodiment.

FIGS. 6A-6D depict a visual workflow of preparing a bone, attaching the punch tool, activating the punch tool, and attaching a cut guide to the bone in accordance with an embodiment.

DETAILED DESCRIPTION

Figure 1:
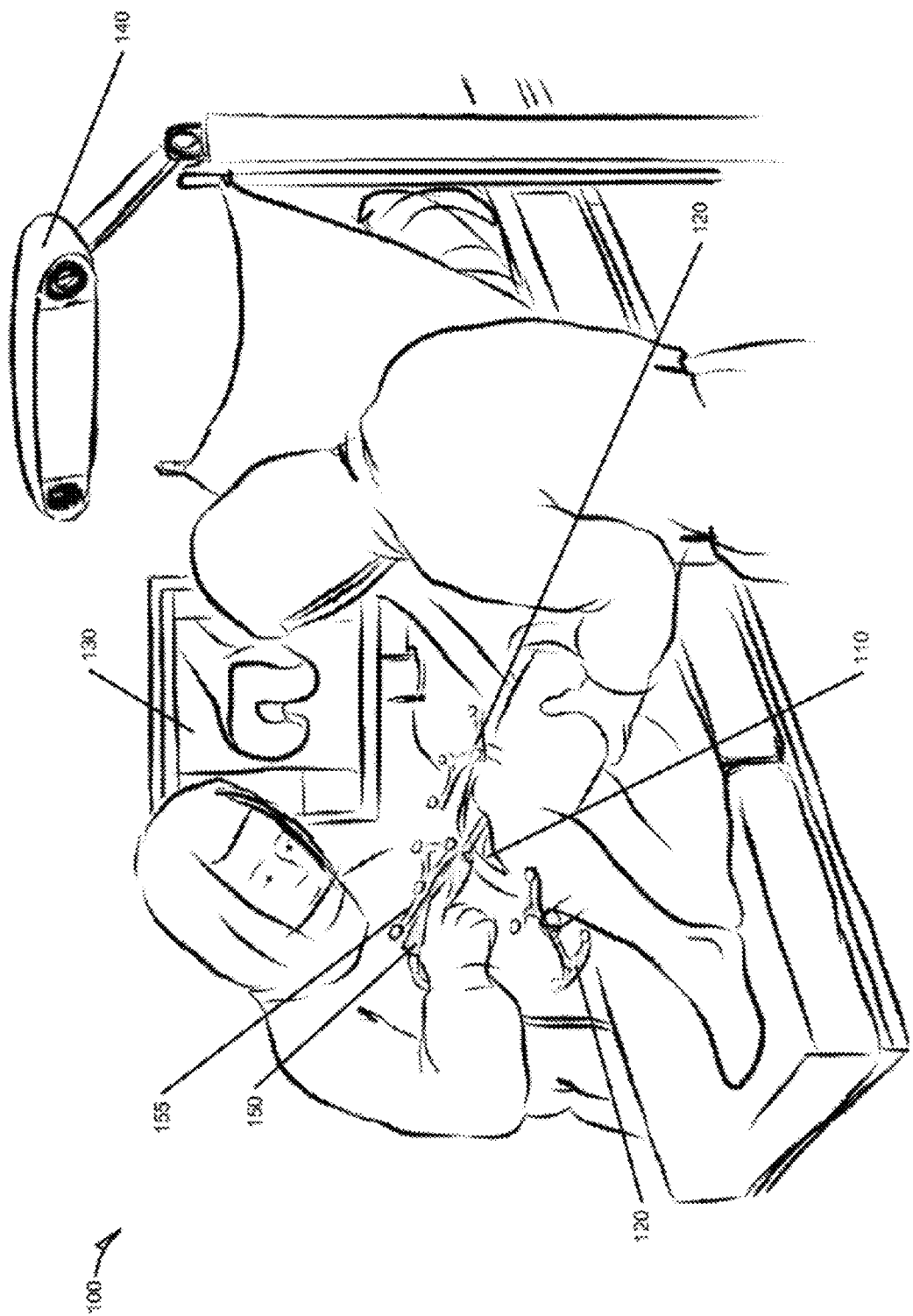
FIG. 1 depicts a diagram illustrating an environment for operating a system for planning and performing robotic-assisted implant surgery in accordance with an embodiment.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

Robotically assisted surgeries, such as Total Knee Arthroplasty (TKA), provide a surgeon with the advantage of planning the procedure and viewing the projected outcome of the procedure prior to performing bone resection. One of the challenges to providing a robotically assisted option is optimizing the workflow efficiency by maintaining continuity with conventional instrumentation. For example, during the manual portion of existing robotically assisted TKA procedures, a set of post holes (e.g., four post holes) are drilled into the patient's femur. A distal cut guide is then fastened to the femur using these post holes to cut the initial distal cut into the femur. A drill guide can then be fastened to the distal cut guide, and two (or more) additional holes can be drilled. The drill guide and distal cut guide can then be removed, and a multi-cut guide block, such as a 5-in-1 cut block, can be attached using the two additional drill holes.

This disclosure describes an improved workflow for positioning and attaching the multi-cut guide block onto the patient's femur. To achieve the improved workflow, this disclosure teaches using a robotically assisted cutting tool to do the initial distal cut in, for example, a femur, eliminating the distal cutting guide. After the distal cut is complete, a punch tool that can be used to produce holes for mounting a multi-cut guide to eliminate the drill guide, thereby reducing the surgical workflow and instrumentation required for the procedure.

In the proposed workflow, the distal cut in the femur is prepared by burring or otherwise cutting the bone under robotic assistance. After preparation of the distal cut (using the robotically controlled cutting device), the surgeon can prepare additional divots located proximate to the position of attachment pins on the multi-cut guide block. For example, the surgeon can prepare two additional divots on the distal cut, a first divot on the medial condyle and a second divot on the lateral condyle. A punch tool can be positioned on the distal cut surface, the punch tool including two reference posts configured to sit within the prepared divots. The surgeon can impact the punch tool to create, for example, two holes positioned to receive the mounting pins on the multi-cut guide block and perform additional bone resection using the mounted multi-cut guide block.

FIG. 1 is an illustration of a system 100 for performing a surgical procedure using a robotic system. The system 100 can include a surgical cutting tool 150 with an associated optical tracking frame 155 (also referred to as tracking array 155), a display device 130, an optical tracking system 140, and patient tracking frames 120 (also referred to as tracking arrays 120). FIG. 1 further illustrates an incision 110 through which a knee replacement surgery can be performed.

In certain implementations, the illustrated robotic surgical system 100 can include a hand-held, computer-controlled surgical robotic system, such as the NAVIO® Surgical System from Blue Belt Technologies, Inc. of Pittsburgh, Pa. NAVIO is a registered trademark of Blue Belt Technologies, Inc. The illustrated robotic system uses an optical tracking system coupled to the robotic controller to track and control a hand-held surgical instrument. For example, the optical tracking system 140 tracks the tracking array 155 coupled to the surgical tool 150 and tracking arrays 120 coupled to the patient to track a location of the instrument relative to the target bone (e.g., femur and tibia for knee procedures).

Figure 2:
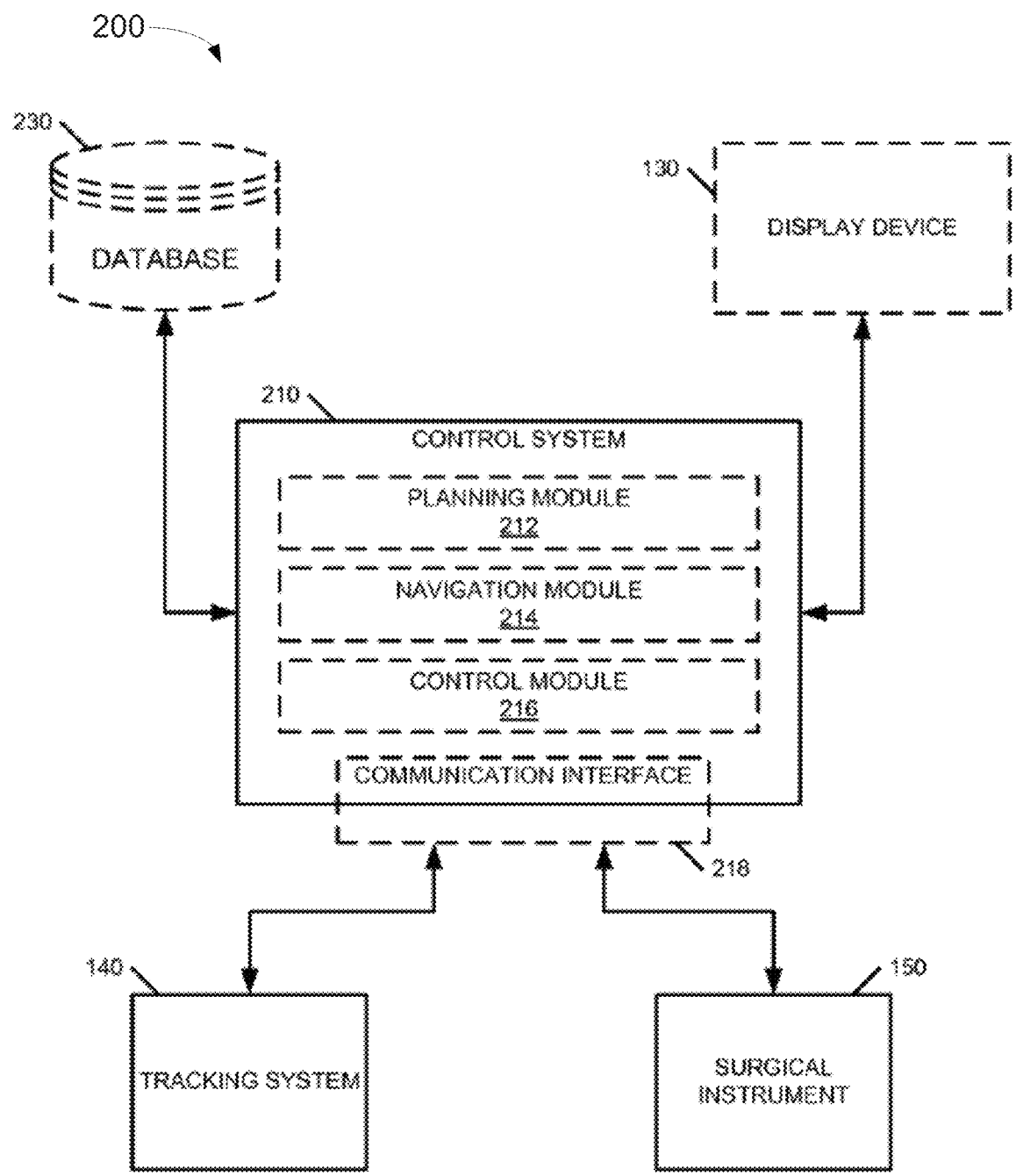
FIG. 2 depicts a block diagram depicting a system for planning and performing implant surgery in accordance with an embodiment.

FIG. 2 is a block diagram depicting an example system 200 for performing a robotically assisted surgical procedure. In certain implementations, the system 200 can include a control system 210, a tracking system 140, and a surgical instrument 150. Optionally, the system 200 also can include a display device 130 and a database 230. In some examples, these components can be combined to provide navigation and control of the surgical instrument 150, which can include navigation and control of a cutting tool or a point probe, among other things, used during an orthopedic prosthetic implant surgery (or similar surgery).

The control system 210 can further include one or more computing devices configured to coordinate information received from the tracking system 140 and provide control to the surgical instrument 150. In an example, the control system 210 can include a planning module 212, a navigation module 214, a control module 216, and a communication interface 218. In certain examples, the planning module 212 can provide pre-operative planning services that allow clinicians the ability to virtually plan a procedure prior to reshaping the target joint during the surgical procedure on the patient. A portion of the planning process performed within the planning module can include operations similar to those discussed in U.S. Pat. No. 6,205,411 titled "Computer-assisted Surgery Planner and Intra-Operative Guidance System," to Digioia et al., which discusses yet another approach to pre-operative planning. U.S. Pat. No. 6,205,411 is hereby incorporated by reference in its entirety.

In some examples, such as a TKA, the planning module 212 can be used to manipulate a virtual model of the implant in reference to a virtual implant host model. The virtual model of the implant host (illustrating the joint to be replaced) can be created through use of a point probe or similar instrument tracked by the optical tracking system 140. In certain implementations, the planning module 212 can collect data from surfaces of the target joint to recreate a virtual model of the patient's actual anatomical structure. Particularly in a joint replacement surgery, this method can increase the accuracy of the planning process by using data collected after the joint has been exposed and without intra-operative imaging. Collecting surface data from the target bone(s) also can allow for iterative reshaping of the target bone to ensure proper fit of the prosthetic implants and optimization of anatomical alignment.

In certain implementations, the navigation module 214 can coordinate tracking the location and orientation of the implant, the implant host, and the surgical instrument 150 during the surgical procedure. In certain examples, the navigation module 214 also may coordinate tracking of the virtual models used during pre-operative or intra-operative planning within the planning module 212. Tracking the virtual models can include operations such as alignment of the virtual models with the implant host through data obtained via the tracking system 140. In these examples, the navigation module 214 can receive input from the tracking system 140 regarding the physical location and orientation of the surgical instrument 150 and an implant host. Tracking of the implant host can include tracking multiple individual bone structures, such as with tracking arrays 120. For example, during a total knee replacement procedure, the tracking system 140 can individually track the femur and the tibia using tracking devices anchored to the individual bones (as illustrated in FIG. 1).

In some examples, the control module 216 can process information provided by the navigation module 214 to generate control signals for controlling the surgical instrument 150. The control module 216 also can work with the navigation module 214 to produce visual animations to assist the surgeon during an operative procedure. Visual animations can be displayed via a display device, such as display device 130. In certain implementations, the visual animations can include real-time 3-D representations of the implant, the implant host, and the surgical instrument 150, among other things. In some examples, the visual animations are color-coded to further assist the surgeon with positioning and orienting the implant.

In certain implementations, the communication interface 218 can facilitate communication between the control system 210 and external systems and devices. The communication interface 218 can include both wired and wireless communication interfaces, such as Ethernet, IEEE 802.11 wireless, or Bluetooth, among others. As illustrated in FIG. 1, the primary external systems connected via the communication interface 218 can include the tracking system 140 and the surgical instrument 150. Although not shown, the database 230 and the display device 130, among other devices, also can be connected to the control system 210 via the communication interface 218. In some examples, the communication interface 218 can communicate over an internal bus to other modules and hardware systems within the control system 210.

In some examples, the tracking system 140 can provide location and orientation information for surgical devices and parts of an implant host's anatomy to assist in navigation and control of semi-active robotic surgical devices. The tracking system 140 can include a tracker (e.g., tracking array 120) that can include or otherwise provide tracking data based on at least three positions and at least three angles. The tracker can include one or more first tracking markers associated with the implant host and one or more second markers associated with the surgical device (e.g., surgical instrument 150). The markers or some of the markers can be one or more of infrared sources, light emitting sources, radio frequency (RF) sources, ultrasound sources, and/or transmitters. As examples, the tracking system 140 can be an infrared tracking system, an optical tracking system, an ultrasound tracking system, an inertial tracking system, a wired system, and/or an RF tracking system. One illustrative tracking system can be the OPTOTRAK® 3-D motion and position measurement and tracking system from Northern Digital, Inc. of Ontario, Canada, although those of ordinary skill in the art will recognize that other tracking systems of other accuracies and/or resolutions can be used. U.S. Pat. No. 6,757,582, titled "Methods and Systems to Control a Shaping Tool," to Brisson et al., provides additional detail regarding the use of tracking systems, such as tracking system 140, within a surgical environment. U.S. Pat. No. 6,757,582 is hereby incorporated by reference in its entirely.

Figure 3B:
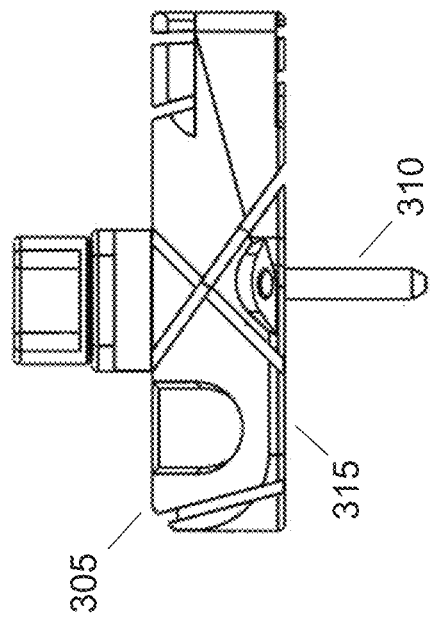
FIGS. 3A and 3B depict a sample bone to be operated on and a surgical guide for use in operating on the sample bone in accordance with an embodiment.
Figure 3A:
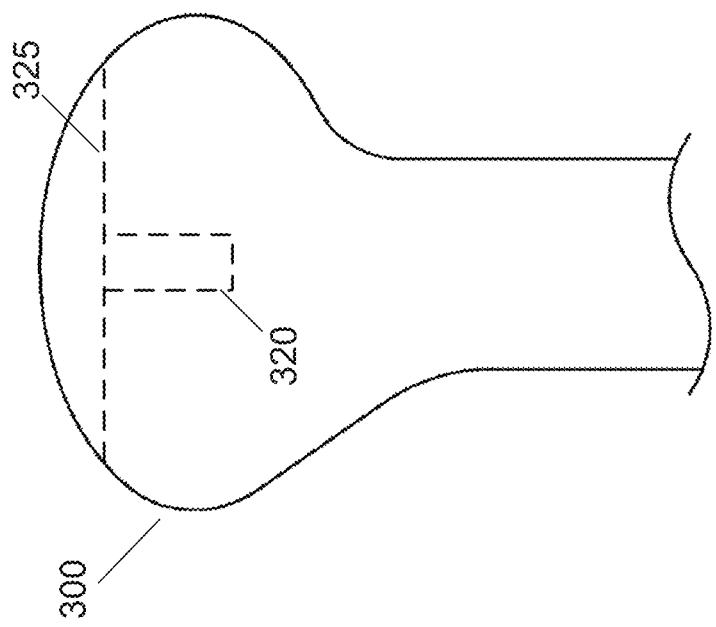

FIGS. 3A and 3B illustrate a sample target bone 300 (e.g., a patient's femur) and a multi-cut guide block 305. In certain implementations, the multi-cut guide block can be a 5-in-1 cut guide for use in TKA as manufactured by Smith & Nephew, Inc. of Memphis, Tenn. However, it should be noted that the 5-in-1 cut guide is provided and described by way of example only, and other types of multi-cut guides can be used with the techniques described herein.

As shown in FIG. 3B, the guide block 305 includes mounting pins 310. To reduce rotation of the guide block 305 once mounted on the target bone 300, multiple mounting pins 310 can be included. However, as guide block 305 is shown in FIG. 3B in a side-profile view, a second mounting pin is positioned behind and hidden by the visible mounting pin 310. The guide block 305 also includes a flat bottom plane 315 configured to interface with a distal cut surface on the target bone 300. In certain implementations, the position of the mounting pins 310 prevent rotational movement of the guide block 305 when inserted into mounting holes, and the interface between the bottom plane 315 and the cut bone prevents lateral movement of the guide block 305.

Referring back to FIG. 3A, dashed lines 320 and 325 indicate areas of bone to be removed to accommodate the guide block 305. For example, line 320 illustrates a hole configured to receive at least one of the mounting pins 310, and line 325 illustrates the distal cut plane configured to interface with the bottom plane 315 of the guide block 305.

Figure 4B:
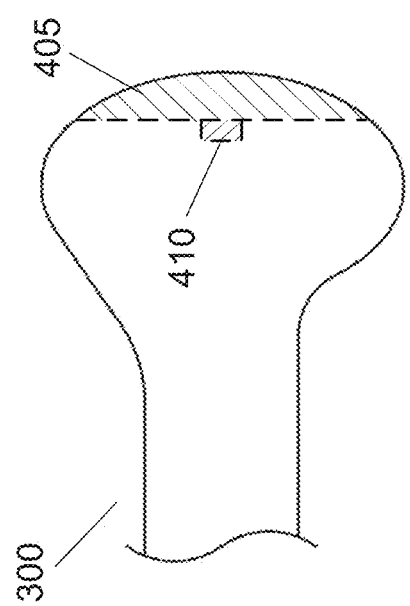
FIGS. 4A and 4B illustrate preparation of a target bone for temporary mounting of a cut guide in accordance with an embodiment.
Figure 4A:
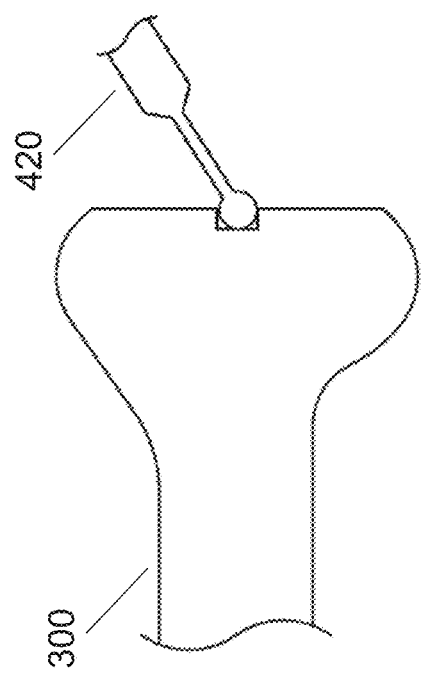

FIGS. 4A and 4B illustrate before and after diagrams of a target bone 300 being prepared for a surgical procedure. In this example, the distal surface of the target bone 300 is resected. Using, for example, a surface preparation tool 420, the surgeon can resect the target bone 300 to remove area 405, thereby defining the distal cut plane (e.g., corresponding to line 325 in FIG. 3A) through the cortical portion of the target bone. However, rather than drill the entire hole (corresponding to line 320 in FIG. 3A), the surgeon can use the surface preparation tool to create one or more divots 410 into the cancellous portion of the target bone 300. The size and shape of a divot 410 can be determined based on, for example, the size and shape of the protruding posts of the punch tool (described in more detail in the discussion of FIGS. 5A and 5B below). A recessed portion of a divot 410 can be in a shape of a cylinder, a cube, a rectangular prism, a triangular prism, a pyramid, a cone, or other three-dimensional shapes. The size and shape of a divot 410 also can be determined based on the location of a landing site for the punch tool and/or guide block, or based on the anatomical, mechanical, and physical properties of the bone and soft tissue at the landing site.

The location of the distal cut plane and the divots 410 can be defined according to the surgical plan as determined by, for example, the planning module 212 as described above. In order to achieve proper bone resection, thereby accurately forming the distal cut plane and the divots 410, the surface preparation tool 420 can be monitored by the tracking system 140 (as described above), and operation of a cutting burr or other cutting interface of the surface preparation tool can be controlled by the control module 216 in response to the currently tracked position of the surface preparation tool.

It should be noted that a spherical cutting burr is shown in FIG. 4B by way of example only, and other shapes, such as a cylindrical or conical cutting burr, can be used for the resection of target bone 300.

In certain implementations, surface preparation tool 420 can include a rotary device including a cutting burr, a surgical drill, a surgical mill, a surgical saw, or other surgical equipment capable of creating the recessed portion on the target bone 300. The surface preparation tool 420 can be operated semi-manually by an operator, such as a surgeon, while it is connected to and monitored by an automated computer-controlled system, such as a precision freehand sculptor (PFS) or other robotic surgical system.

FIGS. 5A and 5B illustrate the punch tool 500 as described herein. As shown in FIG. 5A, the punch tool 500 is in a non-actuated position. The punch tool 500 can include a stationary base component 505. In certain implementations, the base 505 can include a planar bottom 510 configured to sit against the distal cut plane of the target bone (e.g., target bone 300 as described above) as well as posts 515. In some examples, the posts 515 can be configured to extend from the base 505 by about 4.0 mm. In other examples, the posts 515 can be configured to extend about 2.5 mm to about 5.0 mm from the base 505. Similarly, in some implementations, the posts 515 can have a diameter of about 6.5 mm. In some examples, the posts 515 can have a diameter of about 5 mm to about 7.5 mm. Based upon the size of the posts 515, the divots (e.g., divots 410 as described above) can be sized to accept the posts 515. For example, if the posts 515 are extend form the base 505 by about 4.0 mm, and the posts are about 6.5 mm in diameter, the divots can be sized about 4.5 mm deep and 6.5 mm in diameter.

The punch tool 500 can further include an actuation portion 520. The actuation portion 520 can be sized to fit within channels 525 on the base 505, the channels configured to guide the movement of the actuation portion. In certain implementations, the punch tool 500 can further include springs 530 or another device configured to provide a biasing force opposing the movement of the actuation portion 520. It should be noted that springs 530 are shown as coil springs by way of example only.

The actuation portion 520 can include an impact face 535. To actuate the punch tool 500, a surgeon can apply an impact force (e.g., via a slap hammer) to the impact face 535. Such an applied force can move the actuation portion 520 into an actuated position, as shown by FIG. 5B.

As shown in FIG. 5B, when actuated, two sharp pins 540 are exposed from the punch tool 500. The sharp pins 540 are configured to exit the base 505 of the punch tool 500 through the posts 515, thereby penetrating the target bone adjacent to the divots prepared in the target bone. The sharp pins 540 can then penetrate the cancellous bone exposed as a result of the distal cut, thereby forming two holes in the cancellous bone.

The sharp pins 540 can be sized based upon the size of the mounting pins on a corresponding multi-cut guide block (e.g., guide block 305 as described above). For example, the sharp pins 540 can be about 3 mm in diameter and protrude about 18 mm from the base 505 of the punch tool 500. In some implementations, the diameter of the sharp pins 540 can be from about 2.5 mm to about 4 mm. Similarly, in some examples, the sharp pins can protrude about 15 mm to about 20 mm from the base 505 of the punch tool 500.

Additionally, the spacing between the sharp pins 540 can be determined based upon the corresponding multi-cut guide block being used. For example, a multi-cut guide block can have its mounting pins spaced 1.5 inches apart on center. A corresponding punch tool 500 can have similarly spaced sharp pins 540, i.e., 1.5 inches apart. In some implementations, a punch tool 500 can have the sharp pins 540 spaced about 1.25 inches apart to about 1.75 inches apart.

Depending upon the manufacturer of the cut guide, in some examples, each cut guide size in a family or similar product line can have the same sized mounting pins. In such an example, a single punch tool can be used with each size cut guide in the family. For example, each cutting guide in the JOURNEY II family as manufactured by Smith & Nephew, Inc. of Memphis, Tenn., has the same set of mounting pins. JOURNEY is a registered trademark of Smith & Nephew, Inc. Thus, a single sized punch tool can be used with each size of cut guide in the JOURNEY II family. In other implementations, each specific cut guide can have a dedicated and appropriately sized punch tool.

Additionally, the punch tool 500 can include a connection point 545 for attaching a handle to the punch tool for easier manipulation and positioning.

The punch tool 500 as described above can be manufactured from a material or set of materials that facilitate easy cleaning and sterilization through, for example, a steam sterilization process. In certain implementations, the punch tool 500 can be manufactured from titanium, stainless steel, and other similar materials that are commonly used to manufacture tools and guides for use during surgery. In some examples, the punch tool 500 can be designed to have a unibody or single-piece design that is not able to be disassembled. In such a design, similar to that as shown in FIGS. 5A and 5B, an open central space can be included in the design to facilitate cleaning of, for example, the sharp pins 540 when in the retracted position (as shown in FIG. 5A). In other examples, the punch tool 500 can a multi-piece design configured to be taken apart for cleaning and sterilization.

It should be noted that the springs 530 as shown above are provided as a way to keep the punch tool 500 in a retracted position, thereby protecting a user from the sharp pins 540. However, additional retraction mechanisms, such as a ball and detent, can be used to keep the punch tool 500 in a retracted position. Keeping the punch tool 500 in a retracted position also acts to protect the sharp pins 540, thereby reducing the chance of misalignment or damage to the posts.

In an alternative design, the punch tool 500 can be designed such that the springs 530 are configured to promote movement of the actuation portion 520 toward the target bone. For example, the punch tool 500 can include a catch that secures the punch tool in the non-actuated position. Upon activation of a release mechanism, the springs can pull or otherwise apply a force to the actuation portion 520, thereby causing the sharp pins 540 to penetrate the cancellous portion of the target bone. Such a design removes the need for a surgeon to apply a force to the punch tool 500 for actuation of the sharp pins 540.

FIGS. 6A-6D illustrate a visual representation of a target bone being prepared to receive a multi-cut guide using a punch tool according to the techniques described herein.

Figure 6B:
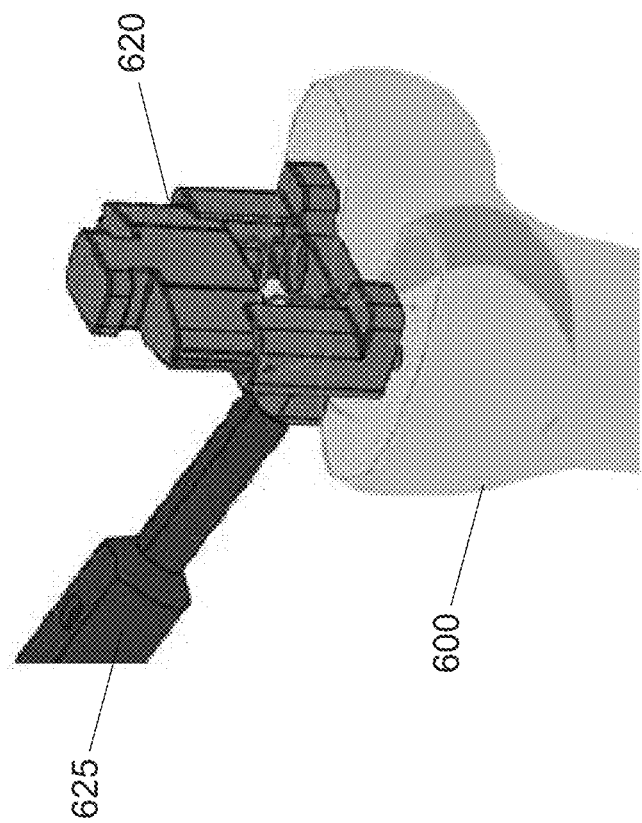
Figure 6A:
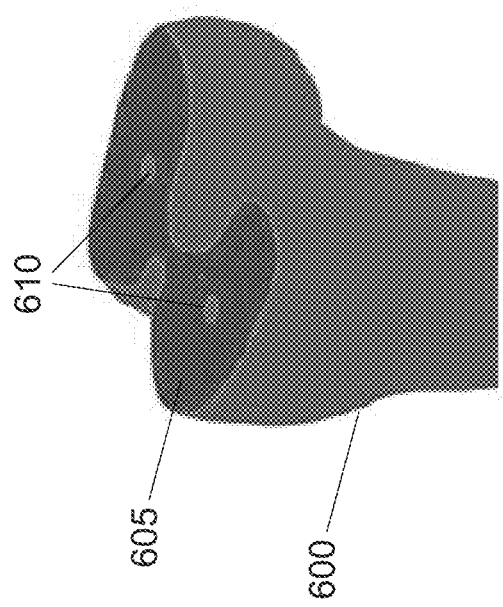

As shown in FIG. 6A, the target bone 600 has been prepared using, for example, a rotary cutting tool or another similar surgical cutting tool according to the process as described above in regard to FIGS. 4A and 4B. As such, target bone 600 has been prepared to include a distal plane cut 605 and divots 610.

Referring to FIG. 6B, a punch tool 620 is positioned on the target bone 600. A bottom surface of the punch tool (e.g., bottom 510 as described above) can be positioned such that it interfaces with the distal cut 605. Additionally, the posts (e.g., posts 515) of the punch tool 620 can be positioned within divots 610 of the target bone 600. As shown in FIG. 6B, the punch tool 620 can include an attached handle 625 to aid in positioning and holding the punch tool in position.

Referring to FIG. 6C, the punch tool 620 has been activated, thereby resulting in sharp posts 630 extending into the target bone 600, creating two holes in the target bone (corresponding to, for example, line 320 as described above in regard to FIG. 3A). Referring to FIG. 6D, the punch tool 620 can be removed from the target bone 600. A multi-cut guide 640 can be positioned on the target bone 600 such that mounting pins 645 fit within the holes created by the sharp posts 630, thereby ensuring that the multi-cut guide is securely and properly positioned on the target bone. The surgeon can further secure the cut guide 640 to the target bone 600 using, for example, 1/8 inch holding pins. The target bone 600 can be further resected using a cutting tool such as an oscillating saw and the multi-cut guide 640.

Figure 7:
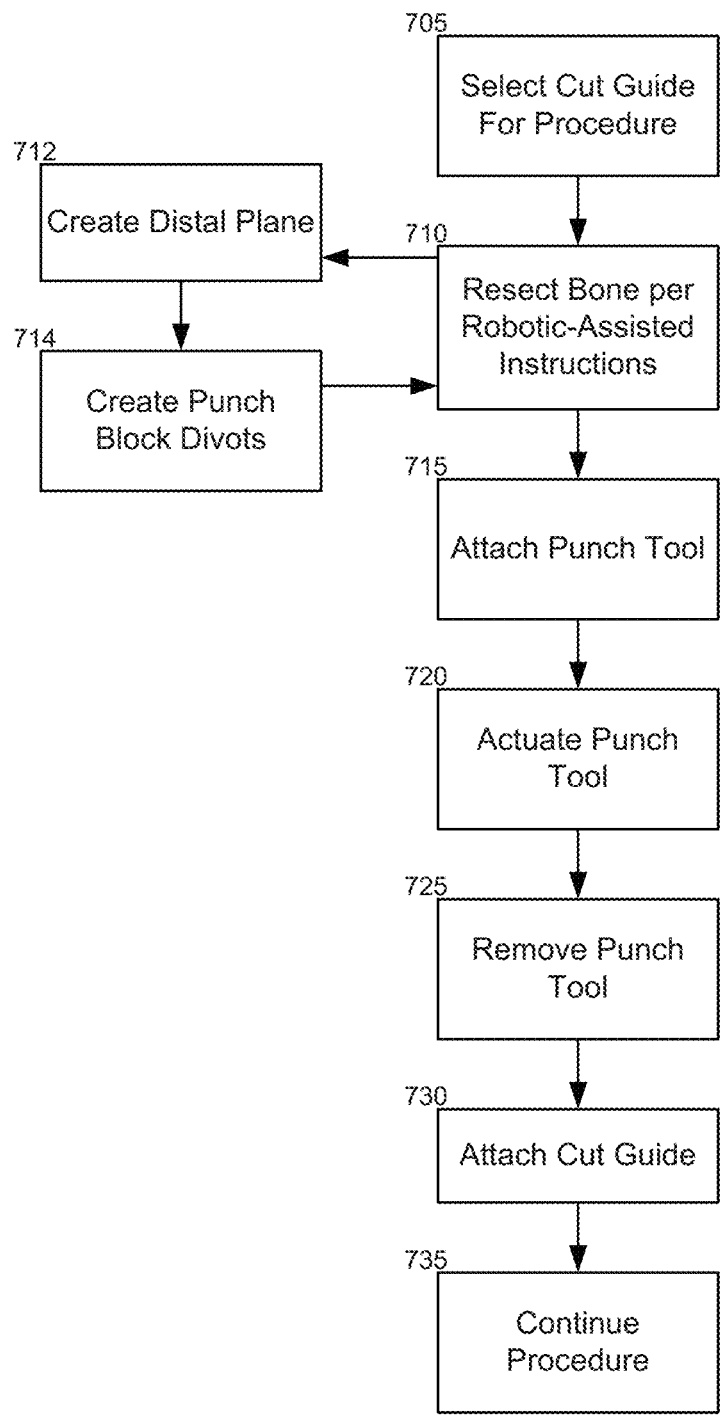
FIG. 7 depicts a process workflow for a surgeon performing the surgical process as shown in FIGS. 6A-6D in accordance with an embodiment.

FIG. 7 illustrates a sample workflow that may be performed by a surgeon performing the surgical process using the punch tool techniques described herein. It is assumed that various initial steps for the surgical procedure have already been performed prior to actual bone resection, such as selecting an implant for implanting into the patient, initial incisions and soft tissue removal, bone surface mapping and imaging, and other similar steps covered, for example, in U.S. Pat. No. 6,205,411 as described above.

Based upon the patient's anatomy (e.g., the size and shape of the patient's femur) and the type of surgery being performed (e.g., a TKA), the surgeon can select 705 a cut guide for use during the procedure. As noted above, based upon the size and shape of the cut guide, each cut guide can have an associated punch tool, or a single punch tool can be adapted to work with a series of cut guides.

The surgeon can provide information related to the selected 705 cut guide to the surgical system (e.g., through the communication interface 218 as described above) and, based upon this information, the surgical system can update the surgery plan. It should be noted that the workflow process for the surgical system is described in greater detail in the following discussion of FIG. 8.

Referring again to FIG. 7, the surgeon can then resect 710 the target bone per the robotic-assisted cutting tool instructions. For example, the surgical system can determine an amount of bone to remove during the resection, and provide control signals to a robotically assisted cutting tool being operated by the surgeon. Depending upon the procedure being performed, the surgeon can be instructed to remove various portions of the target bone. For example, during a TKA, the surgeon can use the robotically assisted cutting tool to create 712 a distal plane. Similarly, the surgeon can create 714 the divots for receiving the punch tool. Following bone resection, the surgeon can attach 715 the punch tool to the target bone. The surgeon can check the position of the punch tool and, upon verifying the punch tool is properly positioned, can actuate 720 the punch tool. The surgeon can remove 725 the punch tool, thereby exposing the holes made by the punch tool. The surgeon can attach 730 the selected cut guide to the holes created by the punch tool, and continue 735 the procedure.

As noted above, in order to assist the surgeon during the procedure described herein as outlined in FIG. 7, a surgical system, such as the control system described above in reference to FIG. 2, can perform various functions as well. For example, FIG. 8 illustrates a sample workflow for a surgical system during a procedure using techniques and processes described herein.

Figure 8:
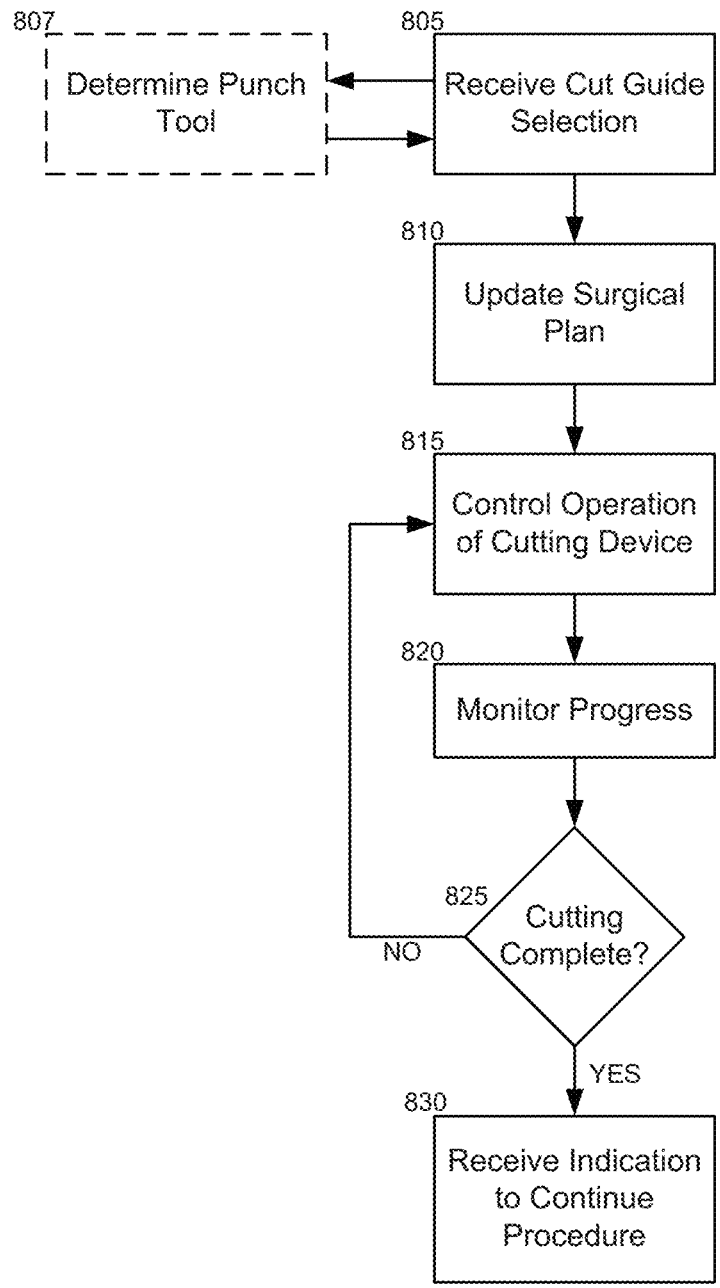
FIG. 8 depicts a process workflow for a computer system assisting in the surgical process as shown in FIGS. 6A-6D in accordance with an embodiment.

Similar to FIG. 7, the description of FIG. 8 assumes that various initial steps for the surgical procedure have already been performed by the surgical system prior to actual bone resection, such as receiving a selection of an implant for implanting into the patient, determining an initial surgical plan for the initial incisions and soft tissue removal, receiving information related to the bone surface mapping and imaging, determining a surgical plan for bone resection, and other similar steps covered, for example, in U.S. Pat. No. 6,205,411 as described above.

Referring to FIG. 8, the surgical system can receive 805 an indication of a cut guide that the surgeon has selected. Based upon the cut guide to be used, the surgical system can optionally determine 807 a punch tool associated with the selected cut guide. Based upon the selected cut guide (and optionally the punch tool), the surgical system can update 810 the surgical plan to determine an amount and location of bone to be removed for the target bone to properly receive the cut guide. Based upon the updated surgical plan, the surgical system can provide the surgeon with a visual indication of the update (e.g., provide a display of the bone to be removed to accommodate the selected cut guide) and can control 815 the operation of a cutting device, ensuring that the surgeon is removing bone according to the surgical plan. As noted above, during control 815 of the cutting device, the surgical system also can track the movement and position of the cutting device to accurately monitor 820 the progress of the bone resection. The surgical system can continually map the amount of bone removed to determine 825 whether the cutting is complete. If the cutting is not complete, the surgical system can continue to control 815 operation of the cutting tool and monitor 820 the process of the bone resection. However, if the surgical system does determine that the cutting is complete, the surgical system can wait while the surgeon performs various manual steps (e.g., placing, actuating and removing the punch tool and placing the cut guide). Upon receiving 830 and indication that the surgeon has completed the manual steps, the surgical system can continue to monitor and assist with the surgical procedure.

It should be noted that, depending upon the capabilities of the tracking system associated with the surgical system, and the design of the punch tool and cut guide, the surgical system can continue to monitor the procedure during the manual steps. For example, if the punch tool and cut guide are configured to include trackable components such as a visual tracking sensor array, the surgical system can monitor the placement of the punch tool and/or the cut guide during the manual steps of the procedure as described herein.

It should be also noted that the above description is generally directed to positioning a femur cutting block by way of example only. The punch tool and associated processes for incorporating the punch tool into a surgical workflow can be applied to any surgical procedure where a bone surface is prepared or otherwise resected to a specific geometry for, for example, accepting an implant component.

Additionally, various alterations to the workflow as described herein are possible. For example, the handle or another component of the punch tool as described herein can be trackable using the tracking system. In such an embodiment, the surgeon can merely prepare the distal cut and, rather than use the divot and post combination as described herein, use the tracking system to determine proper placement of the punch tool prior to actuation.

Figure 9:
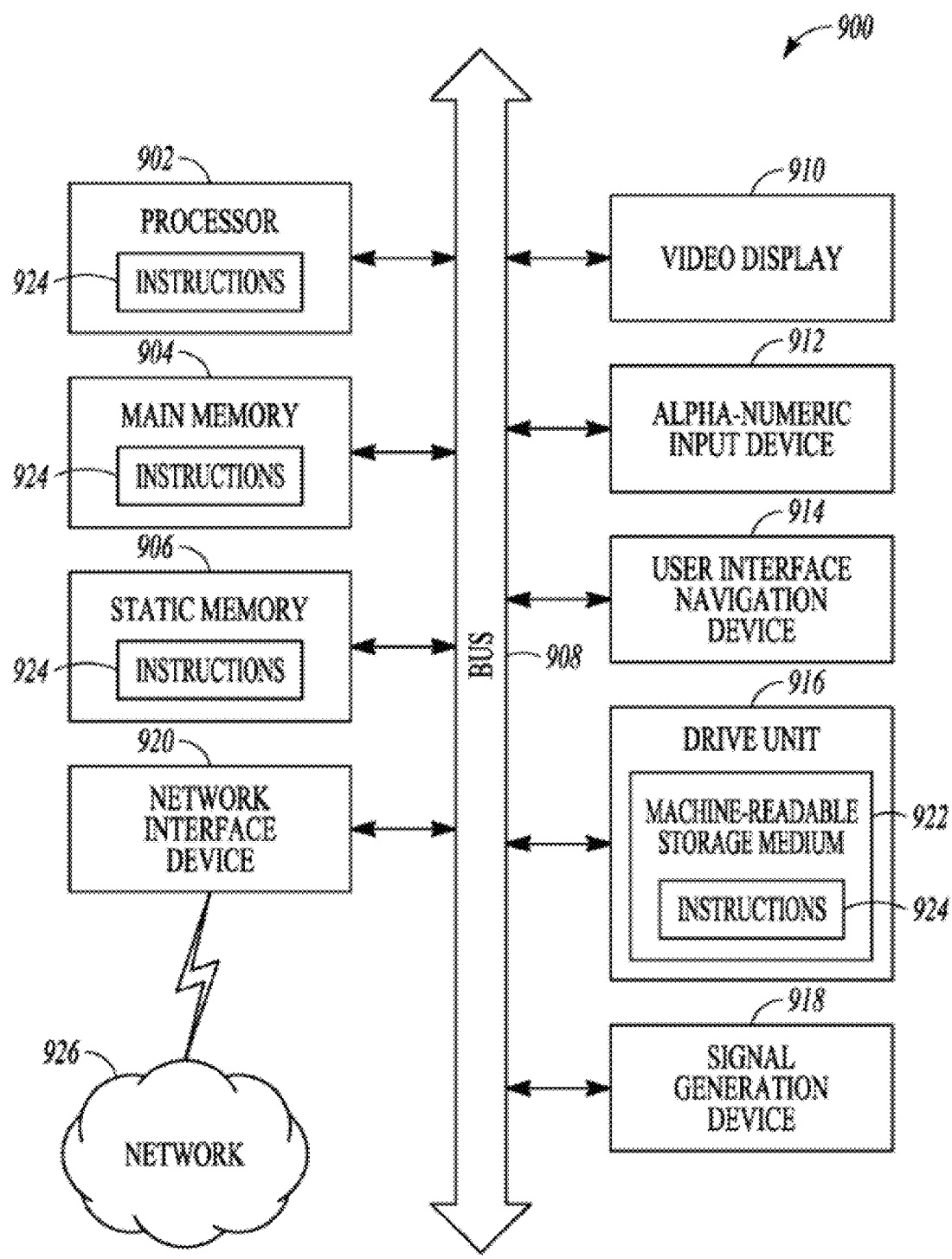
FIG. 9 depicts a computer system for use with the robotically assisted surgical system as described herein.

FIG. 9 is a block diagram that illustrates an example of a machine in the form of a computer system 900 within which instructions, for causing the computer system to perform any one or more of the methods discussed herein, may be executed. In various embodiments, the machine can operate as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a PDA, a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies and/or processes discussed herein.

The example computer system 900 includes a processor 902 (such as a central processing unit (CPU), a graphics processing unit (GPU), or both), a main memory 904 and a static memory 906, which communicate with each other via a bus 908. The computer system 900 may further include a video display unit 910 (such as a liquid crystal display (LCD) or a cathode ray tube (CRT)), an alpha-numeric input device 912 (such as a keyboard), a user interface (UI) navigation device (or cursor control device) 914 (such as a mouse), a disk drive unit 916, a signal generation device 918 (e.g., a speaker) and a network interface device 920.

The disk drive unit 916 includes a machine-readable storage medium 922 on which is stored one or more sets of instructions and data structures (e.g., software) 924 embodying or used by any one or more of the methods or functions described herein. The instructions 924 may also reside, completely or at least partially, within the main memory 904, static memory 906, and/or within the processor 902 during execution thereof by the computer system 900, the main memory 904 and the processor 902 also constituting machine-readable media. In an example, the instructions 924 stored in the machine-readable storage medium 922 include instructions causing the computer system 900 to receive a target bone representation including a data set representing the anatomic structure of the target bone. The instructions 924 can also store the instructions 924 that cause the computer system 900 to generate a cut guide positioning plan for positioning the cut guide onto or conforming to the target bone. The machine-readable storage medium 922 may further store the instructions 924 that cause the computer system 900 to produce the two or more divots sized, shaped or otherwise configured to receive and position the punch tool.

While the machine-readable storage medium 922 is shown in an example embodiment to be a single medium, the term "machine-readable storage medium" may include a single medium or multiple media (e.g., a centralized or distributed database, and/or associated caches and servers) that store the one or more instructions or data structures. The term "machine-readable storage medium" shall also be taken to include any tangible medium that is capable of storing, encoding or carrying instructions for execution by the machine and that cause the machine to perform any one or more of the methods of the present invention, or that is capable of storing, encoding or carrying data structures used by or associated with such instructions. The term "machine-readable storage medium" shall accordingly be taken to include, but not be limited to, solid-state memories, and optical and magnetic media. Specific examples of machine-readable media include non-volatile memory, including by way of example, semiconductor memory devices (e.g., erasable programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks. A "machine-readable storage medium" shall also include devices that may be interpreted as transitory, such as register memory, processor cache, and RAM, among others. The definition provided herein of machine-readable storage medium is applicable even if the machine-readable storage medium is further characterized as being "non-transitory." For example, any addition of "non-transitory," such as non-transitory machine-readable storage medium, is intended to continue to encompass register memory, processor cache and RAM, among other memory devices.

In various examples, the instructions 924 may further be transmitted or received over a communications network 926 using a transmission medium. The instructions 924 may be transmitted using the network interface device 920 and any one of a number of well-known transfer protocols (e.g., HTTP). Examples of communication networks include a LAN, a WAN, the Internet, mobile telephone networks, plain old telephone (POTS) networks, and wireless data networks (e.g., Wi-Fi and WiMAX networks). The term "transmission medium" shall be taken to include any intangible medium that is capable of storing, encoding or carrying instructions for execution by the machine, and includes digital or analog communications signals or other intangible media to facilitate communication of such software.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by $\frac{1}{10}$ of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A surgical punch tool, comprising:
a stationary base component having a planar bottom side and an upper housing comprising one or more channels;
first and second posts spaced apart from each other and extending from the planar bottom side such that the first and second posts are configured to sit against medial and lateral condyles of a femur, respectively, when placed against a resected distal surface of the femur;
a first sharp pin and a second sharp pin separate from the first sharp pin;
an actuation portion received by and moveable within the channels and comprising an impact face; and
first and second springs coupled to the actuation portion and the stationary base component and configured to bias the actuation portion relative to the stationary base component, wherein the actuation portion is configured to simultaneously move the first and second sharp pins from a non-actuated position within the first and second posts, respectively, to an actuated position extending through the stationary base component and from the first and second posts, respectively, in response to impaction of the impact face, to thereby engage the medial and lateral condyles.

2. The surgical punch tool of claim 1, wherein the first and second springs are configured to provide a biasing force opposing movement of the actuation portion towards the stationary base component.

3. The surgical punch tool of claim 1, wherein the first and second springs are configured to provide a biasing force promoting movement of the actuation portion towards the stationary base component.

4. The surgical punch tool of claim 1, wherein each of the first and second posts extends from the stationary base component by about 2.5 mm to about 5 mm.

5. The surgical punch tool of claim 1, wherein each of the first and second posts has a diameter of about 5 mm to about 7.5 mm.

6. The surgical punch tool of claim 1, wherein each of the first and second sharp pins extends from the stationary base component by about 15 mm to about 20 mm in the actuated position.

7. The surgical punch tool of claim 1, wherein each of the first and second sharp pins has a diameter of about 2.5 mm to about 4 mm.

8. The surgical punch tool of claim 1, wherein a center of the first sharp pin is about 1.25 inches to about 1.75 inches away from a center of the second sharp pin.

* * * * *